US006730826B2

(12) United States Patent
Wagner et al.

(10) Patent No.: US 6,730,826 B2
(45) Date of Patent: May 4, 2004

(54) PLANT TRICHOME GLAND SPECIFIC PROMOTER SEQUENCE

(75) Inventors: George J. Wagner, Lexington, KY (US); Susheng Gan, Lexington, KY (US); Erming Wang, Lexington, KY (US); Rui Wang, New York, NY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 09/813,356

(22) Filed: Mar. 21, 2001

(65) Prior Publication Data

US 2003/0100050 A1 May 29, 2003

Related U.S. Application Data

(60) Provisional application No. 60/191,088, filed on Mar. 22, 2000.

(51) Int. Cl.$^7$ .................. C12N 15/82; C12N 15/90; A01H 5/00; A01H 5/10
(52) U.S. Cl. ............... 800/287; 435/320.1; 435/419; 435/468; 536/24.1; 800/288; 800/298
(58) Field of Search ................. 435/69.1, 320.1, 435/410, 419, 468; 536/23.6, 24.1; 800/278, 279, 287, 288, 295, 298, 301, 302

(56) References Cited

PUBLICATIONS

Kim et al, "A 20 nucleotide upstream element is essential for thenopaline synthase (nos) promoter activity", 1994, Plant Molecular Biology vol. 24, pp. 105–117.*

Hsu et al, "Analysis of promoter activity of cotton lipid transfer protein gene LTP6 in transgenic tobacco plants", 1999, Plant Science vol. 143, pp. 63–70.*

Vaeck et al, "transgenic plants protected from insect attack", 1987, Nature vol. 328, pp. 33–37.*

Düring et al, Synthesis and self–assembly of a functional monoclonal antibody in transgenic Nicotiana tabacum, 1990, Plant Molecular Biology, vol. 15, pp. 281–293.*

Del Sorbo et al, "Functional Expression of the Gene cu, Encoding the phytotoxic Hydrophobin Cerato–ulmin, Enables Ophiostoma quercus, a Nonpathogen on Elm, to Cause Symptoms of Dutch Elm Disease", 2000, MPMI vol. 13 No. 1, pp. 43–53.*

Clark et al., "Spatially distinct expression of two new cytochrome P450s in leaves of *Nepeta racemosa:* identification of a trichome–specific isoform", Plant Molecular Biology 33, 1997, pp. 875–885.

G. Hutvagner, et al., "Isolation and sequence analysis of a cDNA and a related gene for cytochrome P450 proteins from *Solanum chacoense*", GENE 188 (1997), pp. 247–252.

* cited by examiner

*Primary Examiner*—Ashwin Mehta
(74) *Attorney, Agent, or Firm*—McDermott, Will & Emery (57) ABSTRACT

The present invention relates to a trichome specific regulatory sequence.

15 Claims, 3 Drawing Sheets

```
-1852 TAAGTTGATAAAGCTAATTTCTCATTTTAGCTACCATCGCTAGTAATCGTGGCAATAACT
-1792 ACCCTAACTATAGCATTTATTGCTACCAAATAAAATTTGGCAGCTAATCATAATTTTTTG
-1732 TCATGAATCAATAGTTATTGTAGCAATAGTTATCTCTTAGCCACAATAAATTATTTAAAA
-1672 TAAAATATTATAGCTAAATAAATATTTTTGCTTTAAGTTCTAAAAGGTTGTGGCAATAGT
-1612 TAAATGATATAGTCACAGATTTATTGGTATAATTGAATTATGTTGCTAATTTCTTAGTTT
-1552 TTTGCCACGAGTTAAAAATTACCAATAGCTATAGTAACTTTTTAATCACAATAAAATATT
-1492 TGAAAGAAAATATTGTAGCTAAATGAATATTTTTTCCTTCAAGTTATTAAAAGTTGTGGC
-1432 AATATAGGTTAAATTAGCCACATGTTTCTTGCTTTAATAGAATTTTGTAGCTAATCATTA
-1372 ACTTTTACCACGAGTTGAACTTAATATAACAACAATAACCTTTTAACCATAATAAAGCGA
-1312 TTTAAATCAAATATTACTAAATAAATAACTTTGCTTTCAAGTTTCTATAAAATCATGGCA
-1252 ATAGTCATTACGATAAAATGATATAACCACGAATATATTGCAACGATAAATTCTGTAACT
-1192 AATCATTAGTTTTTGCGACGAGGTAAATTTTCCGTCACAGTAGCAATCTTCTAGGCACAT
-1132 TAAAAATTTGAAACAAAATTTTGTAGTCAAATAAATATTTATCTTCTTATTTTAAGAAAA
-1072 TAAAAATAGTTAGATAATAGTTACTACTATTTGTCATGAAAATATCAATAGATACAAATT
-1012 TAAAGTGACTATAAATTTACGAGTTTACTATACTTTAGTCGTACAGTTTGCAATAATAGT
 -952 ATTTTAACCACAATTAGTTATATGTACAAAATAACATAAGTGAATAACTTTTTTTCAATG
 -892 AGAAAATAAGAGTTGCTCAAACAATATCAAGTTACAAAAATTTAATTTTAACTGTAAAAG
 -832 TTATATTTTTCCAAAATAACATAAACTATAGTAATTATATATAGTTTGAAGTATTAATAA
 -772 AATTTAAATATGCAAAAGTTAATTTTAATAAACCATTTGTATGCCTAACTTGTAGCCTCT
 -712 AAACTATTTTATTTGCTTTATTTATCAAACTCATATTTTATTTTATTGCACCTTGTTAGT
 -652 TTTGGACGTTAATTATATATATTTGGTGTAAAATTTAAAATATATTAACATTTGTGGAGA
 -592 ATTTATGTATGCCTGGTTCTTAACTATTTTTTTTTATATAACTGGTTAGAGTAATTTCTT
 -532 ATATTTCAGTATTTATTTTTAAATAAGTCCTCATAAATTGAAGACTTTAAAAGTTTTTGT
 -472 GTCATTCCTCTTTTTATTTAAGAAATTGAAGAATTCCGCTAAATTTCATATTTCCGCTGT
 -412 TATTTAACTGTTTATTTCCCTTGTTAATATAATTGGTAAGAAGTTTTAAAATAAAGGAGT
 -352 TAATGATTTTCTAGGTTCATGGCTTGCCTAGCTTCTACGAGTAAGCGCCATCACGACTCC
 -292 CGAGGATAAGGAAATCCGGGTCGTAGCATTCACTCACAAAAATTACTAAAAACAAAGTTT
 -232 ACCCTTCTCCCAAAAGTAAATTTCATATTTGGCTCCACATAATGTGTT*CAAT*GAGTCAAG
 -172 TGAAGTACTTTTCATGACAAAAAAAAGTTGCTGAAAAATGCATATCTCATATTTTTTTTT
 -112 TAGAGAAATC*CCAT*TTCTTGCCTAAACGAAAGCC*TATAAAA*GAGCATATATTGCAACAAC
  -52 AGTTTGCAGAAACTATCAAGTCAAATAATCCCCCCTTTAATTCCCTCCCAAAATGCAGTT
    9 CTTCAACTTCTTTTCCCTTTTCCTTTTTGTGTCATTTCTCTTTTTATTTAAGAAATGGAA
   69 GAATTCCAATAGCCAAACCAAAAGATTGCCTCCAGGTCCATGG
```

PLANT TRICHOME GLAND SPECIFIC PROMOTER SEQUENCE

CONTINUING DATA

This application claims the benefit of priority to U.S. Provisional Application No. 60/191,088, filed Mar. 22, 2000, which is incorporated by reference herein in its entirety.

FIELD OF THE INVENTION

The present invention relates to a trichome specific regulatory sequence such as a promoter, and heterologous constructs comprising the trichome specific regulatory sequence and DNAs encoding a single or multiple polypeptide of interest. The present invention is also related to transgenic expression of a polypeptide(s) of interest in the trichome.

BACKGROUND OF THE INVENTION

Most surfaces of most plants are said to be pubescent, or bearing of trichomes or hairs. The morphology of these structures can vary greatly with tissues and species. Indeed, the botanical literature is said to contain more than 300 descriptions (uniseriate, capitate-sessile, etc.) to characterize various morphological types. These characteristics have often been used in plant classification. Functionally, trichomes may be simple hairs which deter herbivores, guide the path of pollinators or affect photosynthesis, leaf temperature, or water loss through increased light reflectance as in desert species. Or, they may be more specialized tissues (glandular secreting trichomes) whose principal function(s) may be to produce pest- or pollinator-interactive chemicals which are stored or volatilized at the plant surface. It has been suggested that in some desert species the principal role of glandular secreting trichomes is to produce such high levels of exudate that it forms a continuous layer on the plant surface. This layer may increase light reflectance and thereby reduce leaf temperature.

It is the glandular, merocrine, secreting trichome type which often produce and accumulate terpenoid oils that is the focus of this application. Other secretory tissues occurring on or in plants include salt glands, salt hairs, nectary and slime glands, resin ducts, and osmophores (perhaps responsible for fragrances in flowers). Useful modification might be genetic manipulation of an enzyme to alter the chemical nature of exudate for the purpose of enhancing disease resistance, enhancing attractiveness to pollinators, or to expand the metabolism of secretory cells to include synthesis of compounds or intermediates not normally formed. It is important to point out that the potential of secreting trichomes to accumulate exudate is highly significant in certain plants where, under optimal conditions, secreted products can reach a level of 10 to 30% of the dry weight of leaves. Glandular trichome exudates usually contain terpenes and essential oils, as well as lipophilic components not easily stored in large amounts within the cell. Therefore, if it were desirable to manipulate plants to produce or overproduce a compound in this class of biochemicals, the secreting trichome system, which amasses secretions outside of gland cells, may be more amenable to overproduction than one requiring intracellular storage.

Esau, *Plant Anatomy*, John Wiley & Sons, N.Y. has defined trichomes as "epidermal appendages of diverse form, structure and functions . . . represented by protective, supporting, and glandular hairs, by scales, by various papillae, and by absorbing hairs of roots." This definition suggests a close relationship between trichomes and root hairs. From this viewpoint, aerial trichomes and subterranean "trichomes" could be said to cover or nearly cover the surfaces of most plants. However, while trichomes and root hairs may resemble each other in morphology, their genetic determinants may differ. Both trichomes and root hairs develop projections from protodermal cells. Glandular structures of trichomes arise from a series of anticlinal and periclinal divisions to form supporting auxiliary cells and glands as in the case of Cannabis. The appearance of glands atop supporting cells and the occurrence of exudate around gland cells has suggested to most observers that secretions are produced in gland cells and not by other epidermal or subepidermal cells.

Hutvagner et al., *Gene* 188 (1997) 247–252 describes the potato P450 gene. The function, tissue specificity and promoter of this potato gene is not presented or discussed in the paper.

Clark et al., Plant *Molecular Biology* 33 (1997) 875–885 describes another P450 gene isolated *Nepeta racemosa* that hybridizes to RNA from trichomes but not that prepared from leaves stripped of trichomes. This gene shows 36 and 45 to 50% homology to 1–31, protein and DNA levels, respectively. No promoter is described in this paper.

Wagner, *Plant Physiol.* 96 (1991) 675–679 provides some brief background on plant glanded trichomes.

In order to produce genetically engineered polypeptides in trichomes there is a need to make a trichome specific regulatory sequence that allows for targeting of gene expression specifically in trichome glands.

SUMMARY OF THE INVENTION

It is an object of the present invention to provide an isolated nucleic acid molecule comprising:

a polynucleotide set forth in SEQ ID NO:1;

a polynucleotide which is a variant or fragment of the polynucleotide set forth in SEQ ID NO:1, wherein said variant or fragment has trichome specific transcriptional regulatory activity; or a polynucleotide sequence which hybridizes to the polynucleotide of SEQ ID NO:1 under 5×SSC and 42° C. wash conditions.

The nucleic acid may be a polynucleotide comprising the sequence set forth in SEQ ID NO:1. The nucleic acid may further comprise a polynucleotide encoding a polypeptide. The polypeptide may be a disease- or pest-resistance conferring protein. The polypeptide may be a pharmaceutical compound. The polypeptide may function to alter horticultural or food plants. The polypeptide may also be a phytotoxic protein, or a protein highly sensitive to modification during isolation from plant tissue homogenates. Any polypeptide at all can be used with the trichome specific regulatory sequence of the invention. The trichome specific regulatory sequence also encompasses a promoter sequence.

Another object of the invention is to provide a composition comprising a polypeptide made from expression of the above-mentioned nucleic acid, and a trichome gland exudate.

The present invention also relates to a vector comprising a replicable vector and the above-mentioned polynucleotide inserted into said vector.

The vector may be preferably a cloning or expression vector, or a plant vector, preferably a binary vector.

The present invention also relates to a cell containing the above-mentioned vector. Preferably, the cell is a plant cell.

The present invention also provides for a plant comprising the above-mentioned nucleic acid.

The present invention is also related to a method for expressing a polypeptide comprising constructing a vector comprising a trichome specific regulatory sequence and a nucleic acid encoding a polypeptide, and inserting said vector into a plant, wherein said polypeptide is expressed trichome specifically.

BRIEF DESCRIPTION OF THE DRAWINGS

The present invention will become more fully understood from the detailed description given herein below, and the accompanying drawings which are given by way of illustration only, and thus are not limitative of the present invention, and wherein;

FIG. 1(A) shows dissecting microscopic views and (B) shows light microscopic views of T.I. 1068 epidermis showing peltate glandular trichomes. Tissue "C" is epidermis from leaf of a non-transformed plant, and "P-GUS" is epidermis from a similar aged leaf of a plant expressing the GUS reporter gene driven by a trichome-specific promoter. Note the occurrence of GUS stain in glands only. Some slight blue color was also found in the stalk cell immediately attached to the gland. This may represent leakage of stain during tissue fixation, or movement between the gland and the first stalk cell within the vacuolar-tubular continuum. No stain was found in root, stem, or any other tissue (not shown).

FIG. 2 (SEQ ID NO:3) shows a DNA sequence of upstream regulatory region of a tobacco trichome specific promoter (TSP), along with first 111 base pair sequence of the first exon (SEQ ID NO:1). The transcription start point, and the putative translation start are in bold letters and underlined. The putative TATA box and putative CAAT box sequences are italicized and underlined. SEQ ID NO:2 shows the upstream sequence without the protein coding region.

FIG. 3 shows a deletion analysis of the tobacco TSP. The activity of full-length promoter (−1852) was set at 100% and used to define the relative activities of further deletions.

DETAILED DESCRIPTION OF THE INVENTION

Abbreviations

Abbreviations for amino acids used herein are conventionally defined as described herein below unless otherwise indicated.

| Amino Acid | Three-letter abbreviation | One-letter symbol |
|---|---|---|
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Diaminopropionic acid | Dpr | |
| Glutamine | Gln | Q |
| Glutamine acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |

-continued

| Amino Acid | Three-letter abbreviation | One-letter symbol |
|---|---|---|
| Methionine | Met | M |
| Ornithine | Orn | |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Specifically Exemplified Polypeptides

The present invention relates to DNA comprising the trichome specific regulatory sequence operably linked to DNA encoding any polypeptide or multiple polypeptides. The polypeptide can be heterologous, preferably a plant protein, but not necessarily limited to plant proteins. The polypeptide can be a variant or fragment of a polypeptide. Preferably, the polypeptide is expressible in the trichome gland. Expression and recovery from a recombinant organism can be by any convenient method.

Substitutions, Additions and Deletions

As possible variants of the polypeptide, the polypeptide may have additional individual amino acids or amino acid sequences inserted into the polypeptide in the middle thereof and/or at the N-terminal and/or C-terminal ends thereof so long as the polypeptide possesses the desired physical and/or biological characteristics. Likewise, some of the amino acids or amino acid sequences may be deleted from the polypeptide so long as the polypeptide possesses the desired physical characteristics. Amino acid substitutions may also be made in the sequences so long as the polypeptide possesses the desired physical and biochemical characteristics.

Sequence Identity

Two sequences are said to be "identical" if the sequence of residues is the same when aligned for maximum correspondence as described below. The term "complementary" applies to nucleic acid sequences and is used herein to mean that the sequence is complementary to all or a portion of a reference polynucleotide sequence.

Optimal alignment of sequences for comparison can be conducted by the local homology algorithm of Smith and Waterman, *Add. Appl. Math.*, 2:482 (1981), by the homology alignment method of Needleman and Wunsch, *J. Mol. Biol.*, 48:443 (1970), by the search for similarity method of Pearson and Lippman, *Proc. Natl. Acad. Sci. USA*, 85:2444 (1988), or the like. Computer implementations of the above algorithms are known as part of the Genetics Computer Group (GCG) Wisconsin Genetics Software Package (GAP, BESTFIT, BLASTA, FASTA and TFASTA), 575 Science Drive, Madison, Wis.

"Percentage of sequence identity" is determined by comparing two optimally aligned sequences over a comparison window, wherein the portion of the sequence in the comparison window may comprise additions or deletions (i.e. "gaps") as compared to the reference sequence for optimal alignment of the two sequences being compared. The percentage identity is calculated by determining the number of positions at which the identical residue occurs in both sequences to yield the number of matched positions, dividing the number of matched positions by the total number of positions in the window and multiplying the result by 100 to yield the percentage of sequence identity. Total identity is then determined as the average identity over all of the windows that cover the complete query sequence.

Post-translational Modification

Also included within the scope of the present invention are polypeptides or fragments or derivatives thereof which are differentially modified during or after translation, e.g., by glycosylation, proteolytic cleavage, phosphorylation, methylation, amidation of glutamic acid, aspartic acid and C-terminal carboxyl groups.

Fusion Polypeptides

The polypeptide of the present invention may be expressed as a fusion polypeptide or chimeric polypeptide with a second polypeptide as transcriptionally expressed from a single trichome specific regulatory sequence. The second polypeptide will usually impart an additional property or characteristic to the fusion polypeptide which is not possessed by the polypeptide of the present invention.

Production of Recombinant Polypeptide

Recombinant polypeptide can be produced by a process which comprises culturing the transformed cell or microorganism described herein under conditions which allow expression of the polypeptide as transcriptionally regulated from the trichome specific regulatory sequence of the invention, optionally recovering the thus expressed polypeptide and optionally purifying the recovered polypeptide. In processes for the synthesis of the polypeptide, DNA which encodes a polypeptide is ligated into a replicable (reproducible) vector and operably linked to the trichome specific regulatory sequence. The vector is used to transform host cells, and the polypeptide is recovered from the culture. Suitable replicable vectors are selected depending upon the particular host cell chosen. Suitable processes are known in the art and are described, for example, in Sambrook et al, Molecular Cloning: A Laboratory Manual, 2nd Ed. c. 1989 by Cold Spring Harbor Laboratory Press, Cold Spring Harbor, N.Y., Chapters 16, 17 and 18.

The polypeptide produced in this manner may be different from natural polypeptide in that it may be free of other polypeptides or materials which occur in natural polypeptide. The polypeptide produced by recombinant techniques may also contain some small amounts of contaminating materials from the microorganism, cells and/or fermentation system in which it was produced. Thus, the present invention is also directed to these new or isolated polypeptides which are produced under the transcriptional control of the trichome specific regulatory sequence.

Purification of Recombinant Polypeptide

Recombinant polypeptide can be recovered from cultures by lysing the cells to release recombinant polypeptide which is present inside the cells. Initially, cell debris can be separated by centrifugation. The remaining debris and the supernatant are then repeatedly treated with solvents in which the cell debris are soluble but in which the recombinant polypeptide is not soluble to thereby precipitate recombinant polypeptide. These procedures can be repeated and combined with other procedures including filtration, dialysis and/or chromatography to obtain a pure product.

DNA and RNA

The invention encompasses DNA including, but not limited to, that shown in SEQ ID NO:1. including variants and fragments thereof that have trichome specific transcriptional activity. The sequence of the regulator which has actually been sequenced is shown in SEQ ID. NO:1. The present invention also includes genomic DNA containing or comprising the requisite nucleotide sequences as well as corresponding RNA and antisense sequences.

Cloned DNA within the scope of the invention also includes allelic variants of the specific sequences presented in the attached Sequence Listing. An "allelic variant" is a sequence that is a variant from that of the exemplified nucleotide sequence, but represents the same chromosomal locus in the organism. In addition to those which occur by normal genetic variation in a population and perhaps fixed in the population by standard breeding methods, allelic variants can be produced by genetic engineering methods. A preferred allelic variant is one that is found in a naturally occurring organism, including a laboratory strain. Allelic variants are either silent or expressed. A silent allele is one that does not affect the phenotype of the organism. An expressed allele results in a detectable change in the phenotype of the trait represented by the locus.

In addition to the above, the preferred upstream region of the trichome specific upstream region may be located in the −1273 to −1123 upstream of the putative translation initiation site. Thus, in one embodiment, the present invention is directed to utilizing a nucleic acid comprising a nucleic acid that has 75% similarity to the DNA depicted in SEQ ID NO:1 or has such similarity to the −1273 to −1123 region of SEQ ID NO:1. More preferably, there is 80% similarity. Still more preferably, there is 85% similarity. Even more preferably, there is 90% similarity, and most preferably, there is 95% similarity to either the DNA depicted in SEQ ID NO:1 or the DNA in the region of −1273 to −1123 from the putative translation start site of SEQ ID NO:1.

A nucleic acid sequence "encodes" or "codes for" a polypeptide if it directs the expression of the polypeptide referred to. The nucleic acid can be DNA or RNA. Unless otherwise specified, a nucleic acid sequence that encodes a polypeptide includes both the transcribed strand and the mRNA or the DNA representative of the mRNA. An "antisense" nucleic acid is one that is complementary to a strand representative of mRNA, including untranslated portions thereof.

DNA Modification

The DNA is readily modified by substitution, deletion or insertion of nucleotides, thereby resulting in novel DNA sequences. Methods for saturating a particular DNA sequence with random mutations and also for making specific site directed mutations are known in the art; see e.g. Sambrook et al supra, Chapter 15.

Hybridizable Variants

The DNA molecule can comprise a nucleotide sequence of SEQ ID NO:1, or can comprise a nucleotide sequence of a nucleotide sequence that hybridizes to a DNA molecule of SEQ ID NO:1 under salt and temperature conditions equivalent to 5×SSC and 42° C. and that possesses the ability to transcriptionally regulate the expression of a gene specifically in the trichome. See Chapters 11 and 12 of Sambrook et al, supra.

Recombinant DNA Constructs

Recombinant DNA constructs comprising one or more of the DNA or RNA sequences described herein and an additional DNA and/or RNA sequence are also included within the scope of this invention. These recombinant DNA constructs have sequences which do not occur in nature or exist in a form that does not occur in nature or exist in association with other materials that do not occur in nature. The DNA and/or RNA sequences described herein above are "operably linked" with other DNA and/or RNA sequences. DNA regions are operably linked when they are functionally related to each other. For example, DNA for a presequence or secretory leader is operably linked to DNA for a polypeptide if it is expressed as a preprotein which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous (or in close proximity to) and, in the case of secretory leaders, contiguous and in reading phase.

Vectors

The invention is further directed to a replicable vector containing cDNA which codes for a polypeptide and which is capable of expressing the polypeptide under the transcriptional control of a trichome specific regulatory sequence.

The present invention is also directed to a vector comprising a replicable vector and a DNA sequence corresponding to the above-described gene inserted into said vector. The vector may be an integrating or non-integrating vector and is conveniently a plasmid.

Transformed Cells

The invention further relates to a transformed cell or microorganism containing cDNA or a vector which codes for the polypeptide or a fragment or variant thereof and which is capable of expressing the polypeptide.

Plant Cell Expression Systems

Plant Vectors

In plants, transformation vectors capable of introducing DNAs under the control of a trichome specific regulatory sequence are easily designed, and generally contain one or more DNA coding sequences of interest under the transcriptional control of 5' and 3' regulatory sequences. Such vectors generally comprise, operatively linked in sequence in the 5' to 3' direction, a trichome specific promoter sequence that directs the transcription of a downstream heterologous structural DNA in a plant; optionally a 5' non-translated leader sequence; a nucleotide sequence that encodes a protein of interest; and a 3' non-translated region that encodes a polyadenylation signal which functions in plant cells to cause the termination of transcription and the addition of polyadenylate nucleotides to the 3' end of the mRNA encoding said protein. Plant transformation vectors also generally contain a selectable marker. Typical 5'-3' regulatory sequences include a transcription initiation start site, a ribosome binding site, an RNA processing signal, a transcription termination site, and/or a polyadenylation signal. Vectors for plant transformation are described (Schardl et al., Gene 61, 1–14, (1987); Plant Mol Biol., 25:989–994 (1994)). Particularly useful vectors for this invention include, but are not limited to (pKYLX71, pPZP family, pKYLX71-35S2).

Plant Transformation and Regeneration

A variety of different methods can be employed to introduce such vectors into plant trichome, protoplasts, cells, callus tissue, leaf discs, meristems, etc., to generate transgenic plants, including Agrobacterium-mediated transformation, particle gun delivery, microinjection, electroporation, polyethylene glycol-mediated protoplast transformation, liposome-mediated transformation, etc. In general, transgenic plants comprising cells containing and expressing DNAs encoding various enzymes can be produced by transforming plant cells with a DNA construct as described above via any of the foregoing methods; selecting plant cells that have been transformed on a selective medium; regenerating plant cells that have been transformed to produce differentiated plants; and selecting a transformed plant which expresses the enzyme-encoding nucleotide sequence.

The DNAs can be introduced either in a single transformation event (all necessary DNAs present on the same vector), a co-transformation event (all necessary DNAs present on separate vectors that are introduced into plants or plant cells simultaneously), or by independent transformation events (all necessary DNAs present on separate vectors that are introduced into plants or plant cells independently). Traditional breeding methods can subsequently be used to incorporate the entire pathway into a single plant. Specific methods for transforming a wide variety of dicots and obtaining transgenic plants are well documented in the literature.

Successful transformation and plant regeneration have been achieved in the monocots as follows: asparagus (*Asparagus officinalis;* Bytebier et al, Proc. Natl. Acad. Sci. USA, 84:5345 (1987)); barley (*Hordeum vulgarae;* Wan and Lemaux, Plant Physiol., 104:37 (1994)); maize (*Zea mays;* Rhodes et al, Science, 240:204 (1988); Gordon-Kamm et al, Plant Cell, 2:603 (1990); Fromm et al, Bio/Technology, 8:833 (1990); Koziel et al, Bio/Technology, 11:194 (1993)); oats (*Avena saliva;* Somers et al, Bio/Technology, 10:1589 (1992)); orchardgrass (*Dactylic glomerata;* Horn et al, Plant Cell Rep., 7:469 (1988)); rice (*Oryza saliva,* including indica and japonica varieties; Toriyama et al, Bio/Technology,6:10 (1988); Zhang et al, Plant Cell Rep., 7:379 (1988); Luo and Wu, Plant Mol. Biol. Rep., 6:165 (1988); Zhang and Wu, Theor. Appl. Genet., 76:835 (1988); Christou et al, Bio/Technology,9:957 (1991)); rye (*Secale cereale;* De la Pena et al, Nature, 325:274 (1987)); sorghum (*Sorghum bicolor;* Cassas et al, Proc. Natl. Acad. Sci. USA; 90:11212 (1993)); sugar cane (Saccharum spp.; Bower and Birch, Plant J., 2:409 (1992)); tall fescue (*Festuca arundinacea;* Wang et al, Bio/Technology, 10:691 (1992)); turfgrass (*Agrostis palustris; Zhong et al, Plant Cell Rep.,* 13:1 (1993)); and wheat (*Triticum aestinum;* Vasil et al, Bio/Technology, 10:667 (1992); Weeks et al, Plant Physiol., 102:1077 (1993); Becker et al, Plant J., 5:299 (1994)).

Relevant Plants

Particularly useful plants for exploiting the trichome gland specific promoter include plants and ferns of the genuses: Populus, Ermophilia, Lycopersicon, Nicotiana, Cannabis, Pharbitis, Apteria, Psychotria, Mercurialis, Chrysanthemum, Polypodium, Pelargonium, Polytrichiales, Mimulus, Chamomile, Monarda, Solanum, Achillea, Valeriana, Ocimum, Medicago, Aesculus, Newcastelia, Plumbago, Pityrogramma, Phacelia, Avicennia, Tamarix, Frankenia, Limonium, Foeniculum, Thymus, Salvia, Kadsura, Beyeria, Humulus, Mentha, Artemisia, Nepta, Geraea, Pogogstemon, Majorana, Cleome, Cnicus, Parthenium, Ricinocarpos, Parthenium, Hymenaea, Larrea, Primula, Phacelia, Dryopteris, Plectranthus, Cypripedium, Petunia, Datura, Mucuna, Ricinus, Hypericum, Myoporum, Acacia, Diplopeltis, Dodonaea, Halgania, Cyanostegia, Prostanthera, Anthocercis, Olearia, Viscaria. This promoter might also be useful in plants having resin ducts, including members of the genus: Pinus, Picea, Hedera, Heracleum, Dorema, Solidago, Citrus, Eucalyptus, Ruta, Dictamnus, Saururus, Typhonium, or Pseudotsuga.

Production of Transgenic Plants Comprising a Gene or Multiple Genes of Interest

Plant transformation vectors capable of delivering DNA (genomic DNAs, plasmid DNAs, cDNAs, or synthetic DNAs) can be easily designed. Various strategies can be employed to introduce these DNAs to produce transgenic plants capable of biosynthesizing high levels of a gene product of interest including:

1. Transforming individual plants with an encoding DNA of interest. Two or more transgenic plants, each containing one of these DNAs, can then be grown and cross-pollinated so as to produce hybrid plants containing the two DNAs. The hybrid can then be crossed with the remaining transgenic plants in order to obtain a hybrid plant containing all DNAs of interest within its genome.

2. Sequentially transforming plants with plasmids containing each of the encoding DNAs of interest, respectively.
3. Simultaneously cotransforming plants with plasmids containing each of the encoding DNAs, respectively.
4. Transforming plants with a single plasmid containing two or more encoding DNAs of interest.
5. Transforming plants by a combination of any of the foregoing techniques in order to obtain a plant that expresses a desired combination of encoding DNAs of interest.

Traditional breeding of transformed plants produced according to any one of the foregoing methods by successive rounds of crossing can then be carried out to incorporate all the desired encoding DNAs in a single homozygous plant line (Nawrath et al, 1994; PCT International Publication WO 93/02187).

In methods 2 and 3, the use of vectors containing different selectable marker genes to facilitate selection of plants containing two or more different-encoding DNAs is advantageous. Examples of useful selectable marker genes include those conferring resistance to kanamycin, hygromycin, sulphonamides, glyphosate, bialaphos, and phosphinothricin.

Stability of Transgene Expression

As several overexpressed enzymes may be required to produce optimal levels, the phenomenon of co-suppression may influence transgene expression in transformed plants. Several strategies can be employed to avoid this potential problem.

One commonly employed approach is to select and/or screen for transgenic plants that contain a single intact copy of the transgene or other encoding DNA. Agrobacterium-mediated transformation technologies are preferred in this regard.

Inclusion of nuclear scaffold or matrix attachment regions (MAR) flanking a transgene has been shown to increase the level and reduce the variability associated with transgene expression in plants. Flanking a transgene or other encoding DNA with MAR elements may overcome problems associated with differential base composition between such transgenes or encoding DNAs and integration sites, and/or the detrimental effects of sequences adjacent to transgene integration sites.

The use of enhancers from tissue-specific or developmentally-regulated genes may ensure that expression of a linked transgene or other encoding DNA occurs in the appropriately regulated manner.

The use of different combinations of promoters, plastid targeting sequences, and selectable markers in addition to the trichome-specific regulatory sequence, for introduced transgenes or other encoding DNAs can avoid potential problems due to trans-inactivation in cases where pyramiding of different transgenes within a single plant is desired.

Finally, inactivation by co-suppression can be avoided by screening a number of independent transgenic plants to identify those that consistently overexpress particular introduced encoding DNAs. Site-specific recombination in which the endogenous copy of a gene is replaced by the same gene, but with altered expression characteristics, should obviate this problem.

Any of the foregoing methods, alone or in combination, can be employed in order to insure the stability of transgene expression in transgenic plants of the present invention.

The following examples are offered by way of illustration of the present invention, and not by way of limitation.

EXAMPLES

Example 1

A unique method for isolating trichome glands (glands from glanded leaf hairs) was used. A novel cold brushing method was used to prepare trichome glands for subtracting gland versus leaf-minus-gland RNA. Mature leaves (about 40, average length 24 cm) of *Nicotiana tabacum* T.I. 1068 were detached and immediately frozen in the atmosphere above a dry ice-ethanol slush. Once frozen, these were placed on a stainless steel incline, the bottom of which was submerged in a pool of liquid $N_2$. Using a 2 inch hog-hair paint brush—briefly dipped in liquid $N_2$—leaves were brushed (down major veins) to detach glands (some with stalks attached) and propel them into the liquid $N_2$ pool. After filtering through a metal screen into a mortar to remove brush hair pieces, and evaporation of the liquid $N_2$ (to about 2 mL), 100 ml of 2-mercaptoethanol was added and the preparation was ground to a fine powder, maintaining liquid $N_2$ temperature.

Messenger RNA's were isolated from glands and cDNA's were prepared. A commercial subtraction kit (PCR-Select cDNA subtraction kit, CLONETECH LAB) was used to prepare gland-specific cDNA's (subtracted gland cDNA's from leaf-minus-gland cDNA's). Trichome gland unique cDNA's obtained were sequenced. One clone (1–31) showed homology to P450 genes. Northern analysis showed that this partial cDNA hybridized to total RNAs isolated from gland, but not leaf-minus-gland, flower, petal, root or stem-minus-gland total RNA's, indicating its gland specificity.

Genomic clones of 1–31 were isolated using a commercial tobacco genomic library. PCR based walking was used to determine the sequence and gene structure of the full-length genomic clones. A genomic clone of 1–31 shows 63 to 47% identity to the potato P450 at the amino acid and DNA levels, respectively. PCR based walking was used to determine the 5' sequence of the 1–31 gene in order to obtain its promoter.

Figure 1A:
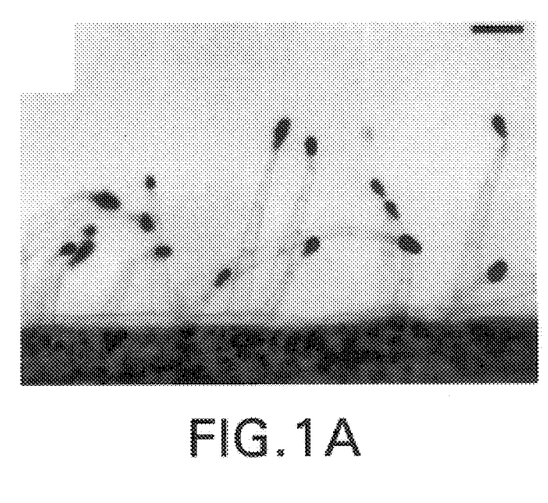
Figure 1B:
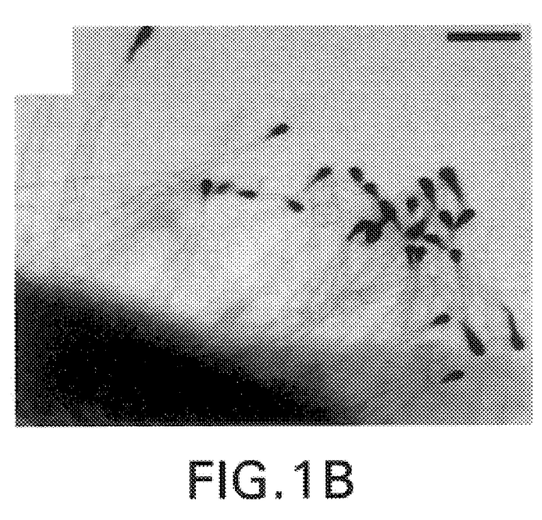

After determining 1852 base pairs, this sequence, along with the coding region +1 to +111, was fused with the beta-glucuronidase (GUS) reporter gene, in frame, and introduced into tobacco. Standard GUS staining of seedlings showed that GUS was expressed trichome-gland-specifically (FIG. 1). In FIG. 1, tissue 'C' is epidermis from leaf of a non-transformed plant, and "P-GUS" is epidermis from a similar aged leaf of a plant expressing the GUS reporter gene driven by the isolated trichome-specificpromoter. Note the occurrence of GUS stain in glands only. Some slight blue color was also found in the stalk cell immediately attached to the gland. This may represent leakage of stain during tissue fixation, or movement between the gland and the first stalk cell within the vacuolar-tubularcontinuum. No stain was found in root, stem, or any other tissue (not shown).

Example 2

We tested the specificity of GUS expression in mature plants to be sure there is no non-gland expression in, e.g., mature roots. The promoter-GUS construct was introduced into petunia, tomato and geranium to test the functionality of the promoter in these non-tobacco, glanded trichome-bearing plants.

Example 3

We transformed tobacco plants with the 1–31 cDNA in antisense orientation. A plant was found that had altered trichome exudate chemistry consistent with a partial knockout of a P450 function. This confirmed the identity of the 1–31 gene. Further, the antisense plant had enhanced insect resistance that is consistent with its altered exudate chemistry.

Example 4

A deletion analysis (promoter dissection) of the upstream region of an isolated trichome specific gene sequence to determine the critical regions of the promoter for trichome gland-specific expression was carried out. Two types of analyses were made of plants expressing 10 deletion constructs plus the full-length construct. First, histochemical staining for GUS indicated that only deletions −1724, −1413, and −1273 had GUS expression in glands. The remainder showed only trace GUS in the trichome stalk cells. Thus, deletion of the −1273 to −1123 region resulted in loss of gland-specific promoter activity. Also the first 111 bp of the first exon (+1 to +111) is essential for gland-specific promoter activity. This was determined in another experiment testing −1852 to +1 with GUS, where no gland-specific activity was found.

Example 5

Figure 3:
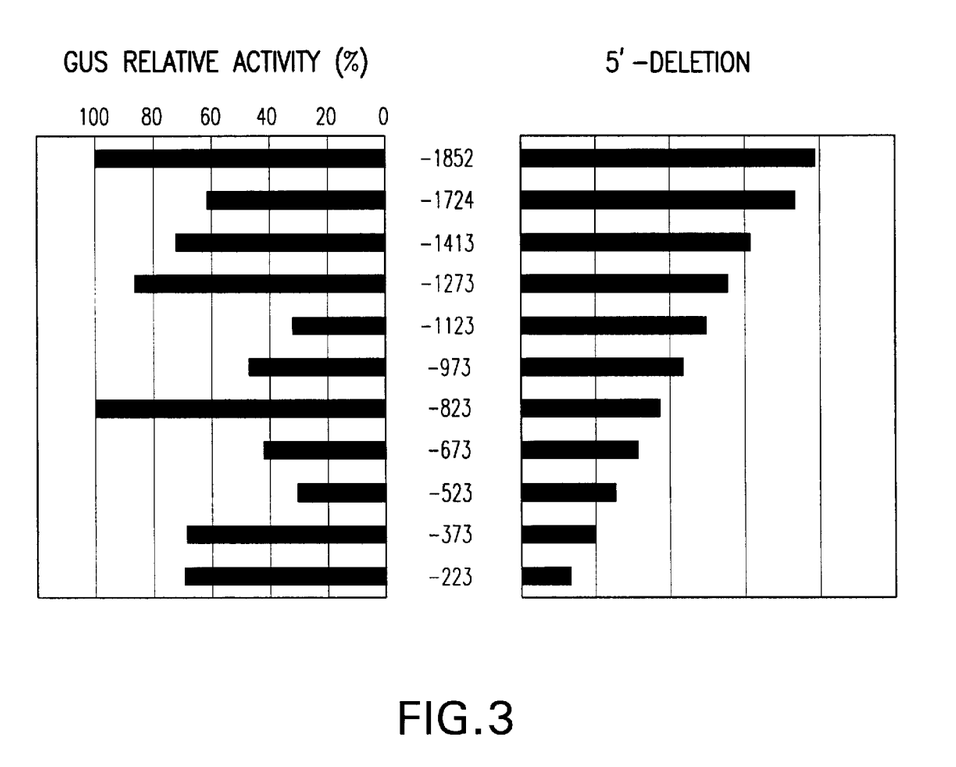

Another deletion analysis involved isolating glands and stalks from leaves of the 10 deletion-GUS plants and the full-length-GUS plant. GUS activity was monitored in homogenates of these using methylumbelliferyl glucuronide (MUG) substrate. Results are shown in FIG. 3. Activities found in deletions −1123, −973, −823, −673, −523, −373, and −223 are attributed to staining in stalk cells and not glands. Thus, results of the histochemical and MUG assays were consistent.

Utility

The DNA of the present invention has various potential uses.

1. Deploy (trichome-gland-specifically)disease- and pest-resistance-conferring proteins at the plant surface to increase resistance.
2. Enhance trichome, natural-product-based pest/disease resistance via trichome-specific metabolic engineering.
3. Empoly trichome glands as "factories" to produce useful secondary products (e.g., pharmaceuticals, flavor and aroma chemicals).
4. Alter fragrance and aroma properties of horticultural and food (spice) plants via trichome-specific metabolic engineering.
5. Employ trichome glands as "factories" to produce foreign proteins (e.g., phytotoxic proteins, proteins highly sensitive to modification during isolation from plant tissue homogenates, etc.)

All of the references cited herein are incorporated by reference in their entirety.

Those skilled in the art will recognize, or be able to ascertain using no more than routine experimentation, many equivalents to the specific embodiments of the invention specifically described herein. Such equivalents are intended to be encompassed in the scope of the following claims.

---

What is claimed is:

1. An isolated nucleic acid molecule comprising:

the polynucleotide sequence set forth in SEQ ID NO: 1; or a fragment of the polynucleotide sequence set forth in SEQ ID NO: 1 comprising bases 578–1963 of SEQ ID NO: 1, wherein SEQ ID NO: 1 and said fragment have plant trichome gland specific transcriptional activity.

2. The nucleic acid molecule of claim 1, which comprises said fragment.

3. The nucleic acid molecule of claim 1, further comprising a polynucleotide sequence encoding a polypeptide.

4. The nucleic acid molecule according to claim 3, wherein said polypeptide is a disease- or pest-resistance conferring protein.

5. The nucleic acid molecule according to claim 3, wherein said polypeptide is a pharmaceutical compound.

6. The nucleic acid molecule according to claim 3, wherein said polypeptide is a phytotoxic protein.

7. A vector, comprising:
the isolated nucleic acid molecule of claim 1.

8. The vector of claim 7, which is an expression vector.

9. The vector of claim 7, which is a plant vector.

10. A host cell containing the vector of claim 7.

11. The host cell of claim 10, which is a plant cell.

12. A transgenic plant comprising the nucleic acid molecule of claim 1.

13. A transgenic seed comprising the nucleic acid molecule of claim 1.

14. A method for expressing a polypeptide comprising:

constructing a vector comprising the isolated nucleic acid molecule of claim 1 operably linked to a nucleic acid encoding a polypeptide; and inserting said vector into a plant, wherein said polypeptide is expressed trichome gland specifically.

15. The transgenic plant of claim 12, wherein the transgenic plant is a food plant or horticultural plant.

* * * * *

SEQUENCE LISTING

```
<160> NUMBER OF SEQ ID NOS: 3

<210> SEQ ID NO 1
<211> LENGTH: 1963
<212> TYPE: DNA
<213> ORGANISM: Nicotiana tabacum
<220> FEATURE:
<221> NAME/KEY: exon
<222> LOCATION: (1853)..(1963)
<221> NAME/KEY: CAAT_signal
<222> LOCATION: (1669)..(1672)
<221> NAME/KEY: TATA_signal
<222> LOCATION: (1775)..(1778)
<221> NAME/KEY: GC_signal
<222> LOCATION: (1806)..(1807)
<221> NAME/KEY: promoter
<222> LOCATION: (1)..(1852)

<400> SEQUENCE: 1
taagttgata aagctaattt ctcattttag ctaccatcgc tagtaatcgt ggcaataact      60
accctaacta tagcatttat tgctaccaaa taaaatttgg cagctaatca taattttttg    120
tcatgaatca atagttattg tagcaatagt tatctcttag ccacaataaa ttatttaaaa    180
taaaatatta tagctaaata aatattttg ctttaagttc taaaaggttg tggcaatagt     240
taaatgatat agtcacagat ttattggtat aattgaatta tgttgctaat ttcttagttt    300
tttgccacga gttaaaaatt accaatagct atagtaactt tttaatcaca ataaaatatt    360
tgaaagaaaa tattgtagct aaatgaatat tttttccttc aagttattaa aagttgtggc    420
aatataggtt aaattagcca catgtttctt gctttaatag aattttgtag ctaatcatta    480
acttttacca cgagttgaac ttaatataac aacaataacc ttttaaccat aataaagcga    540
tttaaatcaa atattactaa ataaataact ttgctttcaa gtttctataa aatcatggca    600
```

-continued

```
atagtcatta cgataaaatg atataaccac gaatatattg caacgataaa ttctgtaact      660
aatcattagt ttttgcgacg aggtaaattt tccgtcacag tagcaatctt ctaggcacat      720
taaaaatttg aaacaaaatt ttgtagtcaa ataaatattt atcttcttat tttaagaaaa      780
taaaaatagt tagataatag ttactactat ttgtcatgaa aatatcaata gatacaaatt      840
taaagtgact ataaatttac gagtttacta tactttagtc gtacagtttg caataatagt      900
attttaacca caattagtta tatgtacaaa ataacataag tgaataactt tttttcaatg      960
agaaaataag agttgctcaa acaatatcaa gttacaaaaa tttaatttta actgtaaaag     1020
ttatattttt ccaaaataac ataaactata gtaattatat atagtttgaa gtattaataa     1080
aatttaaata tgcaaaagtt aattttaata aaccatttgt atgcctaact tgtagcctct     1140
aaactatttt atttgcttta tttatcaaac tcatatttta ttttattgca ccttgttagt     1200
tttggacgtt aattatatat atttggtgta aaatttaaaa tatattaaca tttgtggaga     1260
atttatgtat gcctggttct taactatttt tttttatata actggttaga gtaatttctt     1320
atatttcagt atttatttt aaataagtcc tcataaattg aagactttaa aagtttttgt     1380
gtcattcctc ttttttattta agaaattgaa gaattccgct aaatttcata tttccgctgt     1440
tatttaactg tttatttccc ttgttaatat aattggtaag aagttttaaa ataaaggagt     1500
taatgatttt ctaggttcat ggcttgccta gcttctacga gtaagcgcca tcacgactcc     1560
cgaggataag gaaatccggg tcgtagcatt cactcacaaa aattactaaa acaaagttt     1620 acccttctcc caaaagtaaa tttcatattt ggctccacat aatgtgttca atgagtcaag     1680
tgaagtactt ttcatgacaa aaaaagttg ctgaaaatg catatctcat attttttttt     1740
tagagaaatc ccatttcttg cctaaacgaa agcctataaa agagcatata ttgcaacaac     1800
agtttgcaga aactatcaag tcaaataatc ccccctttaa ttccctccca aa atg cag    1858
                                                            Met Gln
                                                              1
```

| ttc ttc aac ttc ttt tcc ctt ttc ctt ttt gtg tca ttt ctc ttt tta | 1906 |
|---|---|
| Phe Phe Asn Phe Phe Ser Leu Phe Leu Phe Val Ser Phe Leu Phe Leu | |
| 5 10 15 | |

| ttt aag aaa tgg aag aat tcc aat agc caa acc aaa aga ttg cct cca | 1954 |
|---|---|
| Phe Lys Lys Trp Lys Asn Ser Asn Ser Gln Thr Lys Arg Leu Pro Pro | |
| 20 25 30 | |

| ggt cca tgg | 1963 |
|---|---|
| Gly Pro Trp | |
| 35 | |

<210> SEQ ID NO 2
<211> LENGTH: 1852
<212> TYPE: DNA
<213> ORGANISM: Nicotiana tabacum
<220> FEATURE:
<221> NAME/KEY: promoter
<222> LOCATION: (1)..(1852)
<221> NAME/KEY: CAAT_signal
<222> LOCATION: (1669)..(1672)
<221> NAME/KEY: GC_signal
<222> LOCATION: (1806)..(1807)

<400> SEQUENCE: 2

```
taagttgata aagctaattt ctcattttag ctaccatcgc tagtaatcgt ggcaataact       60
accctaacta tagcatttat tgctaccaaa taaaatttgg cagctaatca taattttttg      120
tcatgaatca ataGTtattg tagcaatagt tatctcttag ccacaataaa ttatttaaaa      180
taaaatatta tagctaaata aatatttttg ctttaagttc taaaaggttg tggcaatagt      240
```

-continued

| | |
|---|---|
| taaatgatat agtcacagat ttattggtat aattgaatta tgttgctaat ttcttagttt | 300 |
| tttgccacga gttaaaaatt accaatagct atagtaactt tttaatcaca ataaaatatt | 360 |
| tgaaagaaaa tattgtagct aaatgaatat tttttccttc aagttattaa agttgtggc | 420 |
| aatataggtt aaattagcca catgtttctt gctttaatag aattttgtag ctaatcatta | 480 |
| acttttacca cgagttgaac ttaatataac aacaataacc ttttaaccat aataaagcga | 540 |
| tttaaatcaa atattactaa ataaataact ttgctttcaa gtttctataa aatcatggca | 600 |
| atagtcatta cgataaaatg atataaccac gaatatattg caacgataaa ttctgtaact | 660 |
| aatcattagt ttttgcgacg aggtaaattt tccgtcacag tagcaatctt ctaggcacat | 720 |
| taaaaatttg aaacaaaatt ttgtagtcaa ataaatattt atcttcttat tttaagaaaa | 780 |
| taaaaatagt tagataatag ttactactat ttgtcatgaa aatatcaata gatacaaatt | 840 |
| taaagtgact ataaatttac gagtttacta tactttagtc gtacagtttg caataatagt | 900 |
| attttaacca caattagtta tatgtacaaa ataacataag tgaataactt ttttttcaatg | 960 |
| agaaaataag agttgctcaa acaatatcaa gttacaaaaa tttaatttta actgtaaaag | 1020 |
| ttatatttt ccaaaataac ataaactata gtaattatat atagtttgaa gtattaataa | 1080 |
| aatttaaata tgcaaaagtt aatttttaata aaccatttgt atgcctaact tgtagcctct | 1140 |
| aaactatttt atttgcttta tttatcaaac tcatatttta tttattgca ccttgttagt | 1200 |
| tttggacgtt aattatatat atttggtgta aaatttaaaa tatattaaca tttgtggaga | 1260 |
| atttatgtat gcctggttct taactatttt tttttatata actggttaga gtaatttctt | 1320 |
| atatttcagt atttattttt aaataagtcc tcataaattg aagactttaa aagttttttgt | 1380 |
| gtcattcctc ttttttattta agaaattgaa gaattccgct aaatttcata tttccgctgt | 1440 |
| tatttaactg tttatttccc ttgttaatat aattggtaag aagttttaaa ataaaggagt | 1500 |
| taatgatttt ctaggttcat ggcttgccta gcttctacga gtaagcgcca tcacgactcc | 1560 |
| cgaggataag gaaatccggg tcgtagcatt cactcacaaa aattactaaa acaaagtttt | 1620 |
| acccttctcc caaagtaaa tttcatattt ggctccacat aatgtgttca atgagtcaag | 1680 |
| tgaagtactt ttcatgacaa aaaaagttg ctgaaaaatg catatctcat attttttttt | 1740 |
| tagagaaatc ccatttcttg cctaaacgaa agcctataaa agagcatata ttgcaacaac | 1800 |
| agtttgcaga aactatcaag tcaaataatc cccccttttaa ttccctccca aa | 1852 |

<210> SEQ ID NO 3
<211> LENGTH: 1963
<212> TYPE: DNA
<213> ORGANISM: Nicotiana tabacum

<400> SEQUENCE: 3

| | |
|---|---|
| taagttgata aagctaattt ctcatttttag ctaccatcgc tagtaatcgt ggcaataact | 60 |
| accctaacta tagcatttat tgctaccaaa taaaatttgg cagctaatca taatttttg | 120 |
| tcatgaatca atagttattg tagcaatagt tatctcttag ccacaataaa ttatttaaaa | 180 |
| taaaatatta tagctaaata atatttttg ctttaagttc taaaaggttg tggcaatagt | 240 |
| taaatgatat agtcacagat ttattggtat aattgaatta tgttgctaat ttcttagttt | 300 |
| tttgccacga gttaaaaatt accaatagct atagtaactt tttaatcaca ataaaatatt | 360 |
| tgaaagaaaa tattgtagct aaatgaatat tttttccttc aagttattaa agttgtggc | 420 |
| aatataggtt aaattagcca catgtttctt gctttaatag aattttgtag ctaatcatta | 480 |
| acttttacca cgagttgaac ttaatataac aacaataacc ttttaaccat aataaagcga | 540 |

```
tttaaatcaa atattactaa ataaataact ttgctttcaa gtttctataa aatcatggca    600
atagtcatta cgataaaatg atataaccac gaatatattg caacgataaa ttctgtaact    660
aatcattagt ttttgcgacg aggtaaattt tccgtcacag tagcaatctt ctaggcacat    720
taaaaatttg aaacaaaatt ttgtagtcaa ataaatattt atcttcttat tttaagaaaa    780
taaaaatagt tagataatag ttactactat ttgtcatgaa aatatcaata gatacaaatt    840
taaagtgact ataaatttac gagtttacta tactttagtc gtacagtttg caataatagt    900
attttaacca caattagtta tatgtacaaa ataacataag tgaataactt tttttcaatg    960
agaaaataag agttgctcaa acaatatcaa gttacaaaaa tttaatttta actgtaaaag   1020
ttatattttt ccaaaataac ataaactata gtaattatat atagtttgaa gtattaataa   1080
aatttaaata tgcaaaagtt aattttaata aaccatttgt atgcctaact tgtagcctct   1140
aaactatttt atttgcttta tttatcaaac tcatatttta ttttattgca ccttgttagt   1200
tttggacgtt aattatatat atttggtgta aaatttaaaa tatattaaca tttgtggaga   1260
atttatgtat gcctggttct taactatttt tttttatata actggttaga gtaatttctt   1320
atatttcagt atttattttt aaataagtcc tcataaattg aagactttaa aagttttttgt   1380
gtcattcctc tttttattta agaaattgaa gaattccgct aaatttcata tttccgctgt   1440
tatttaactg tttatttccc ttgttaatat aattggtaag aagtttaaa ataaaggagt    1500
taatgatttt ctaggttcat ggcttgccta gcttctacga gtaagcgcca tcacgactcc   1560
cgaggataag gaaatccggg tcgtagcatt cactcacaaa aattactaaa aacaaagttt   1620
acccttctcc caaagtaaa tttcatattt ggctccacat aatgtgttca atgagtcaag    1680
tgaagtactt ttcatgacaa aaaaagttg ctgaaaaatg catatctcat attttttttt    1740
tagagaaatc ccatttcttg cctaaacgaa agcctataaa agagcatata ttgcaacaac   1800
agtttgcaga aactatcaag tcaaataatc cccccttttaa ttccctccca aaatgcagtt   1860
cttcaacttc ttttcccttt tccttttttgt gtcatttctc tttttattta agaaatggaa   1920
gaattccaat agccaaacca aaagattgcc tccaggtcca tgg                      1963
```